US00PP37157P2

(12) United States Plant Patent
Jackson et al.

(10) Patent No.: US PP37,157 P2
(45) Date of Patent: Dec. 16, 2025

(54) ***CERCIS* PLANT NAMED 'JN31'**

(50) Latin Name: *Cercis canadensis*
Varietal Denomination: JN31

(71) Applicants: Ray Jackson, Belvidere, TN (US); Cindy Jackson, Belvidere, TN (US)

(72) Inventors: Ray Jackson, Belvidere, TN (US); Cindy Jackson, Belvidere, TN (US)

(73) Assignee: GREENLEAF NURSERY CO., Park Hill, OK (US)

( * ) Notice: Subject to any disclaimer, the term of this patent is extended or adjusted under 35 U.S.C. 154(b) by 0 days.

(21) Appl. No.: 18/799,927

(22) Filed: Aug. 9, 2024

(51) Int. Cl.
*A01H 5/12* (2018.01)
*A01H 6/54* (2018.01)

(52) U.S. Cl.
USPC ..... Plt./216

(58) Field of Classification Search
USPC ..... Plt./216
CPC . A01H 5/012; A01H 5/02; A01H 5/00; A01H 6/54
See application file for complete search history.

(56) References Cited

PUBLICATIONS

Facebook North Texas Gardening 2024 retrieved on Apr. 9, 2025 at https://www.facebook.com/groups/northtexasgardening/posts/6697787826990508/, one page. (Year: 2024).*
Issuu Garden Debut New Varieties Catalog 2023-2024, retrieved on Apr. 9, 2025 at https://issuu.com/gardendebut/docs/2023-24_gd_new_varieties_catalog, cover page and p. 14. (Year: 2023).*
Plant Me Green, retrieved on Apr. 9, 2025 at https://plantmegreen.com/products/redbud-rise-n-shine?srsltid=AfmBOoo7hAMbhlueLAPSpamVteU4erTQ72N2vTvK7VveMwHEuQUYizFI, 4 pp. (Year: 2025).*
Virginia Nursery & Landscape Association 2023 Guide to Virginia Growers, retrieved on Apr. 9, 2025 at https://vnla.org/wp-content/uploads/2022/12/vnla-growers-guide-2023.pdf, pp. 1-5 and 13 (Year: 2023).*

* cited by examiner

*Primary Examiner* — June Hwu
(74) *Attorney, Agent, or Firm* — Penny J. Aguirre

(57) ABSTRACT

A new cultivar of *Cercis canadensis* tree named 'JN31' that is characterized by its foliage colors that emerge bright yellow in color and change to chartreuse green in color when they mature, its foliage that is resistant to sun scorch in summer in Southern climates, its strong, upright branching habit, its tolerance to wind and ice damage, and its early winter dormancy with low winter injury.

2 Drawing Sheets

Botanical classification: *Cercis canadensis*.
Variety denomination: 'JN31'.

CROSS-REFERENCE TO RELATED APPLICATIONS

This application is co-pending with U.S. Plant Patent Applications filed for plants derived from the same breeding program that are entitled *Cercis* Tree Named 'JN100' (U.S. Plant Pat. No. 36,785. *Cercis* Tree Named 'JN104' (U.S. Plant patent application Ser. No. 18/799,948), and *Cercis* Tree Named 'JN106' (U.S. Plant patent application Ser. No. 18/799,953).

The present invention relates to a new and distinct cultivar of *Cercis canadensis* and will be referred to hereafter by its cultivar name, 'JN31'. 'JN31' is an Eastern redbud tree grown for use as a landscape plant.

The Inventors discovered the new cultivar in summer of 2015 as a naturally occurring branch mutation of *Cercis canadensis* 'JN2' (U.S. Plant Pat. No. 21,451) in a field at their nursery in Belvidere, Tennessee.

Asexual propagation of the new cultivar was first accomplished by budding onto seedling rootstock of *Cercis canadensis* by one of the Inventors in August of 2017 in Belvidere, Tennessee. Asexual propagation by budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'JN31' as a unique cultivar of *Cercis*.

1. 'JN31' exhibits foliage colors that emerge bright yellow in color and change to chartreuse green in color when they mature.
2. 'JN31' exhibits foliage that is resistant to sun scorch in summer in Southern climates.
3. 'JN31' exhibits a strong, upright branching habit.
4. 'JN31' exhibits tolerance to wind and ice damage.
5. 'JN31' exhibits early winter dormancy with low winter injury.

The parent plant of 'JN31', 'JN2', is similar to 'JN31' in having new foliage that is yellow in color. 'JN2' differs from 'JN31' in having a less upright branching habit, foliage that becomes flushed with apricot color tones and is prone to sun scorch in summer climates and more winter damage. 'JN31' can be compared to the *Cercis canadensis* cultivar 'Hearts of Gold' (U.S. Plant Pat. No. 17,740). 'Hearts of Gold' is similar to 'JN31' in having young bright yellow emerging foliage in spring. 'Hearts of Gold' differs from 'JN31' in having foliage that emerges suffused with orange-red in color and matures to bright gold in color, and in being susceptible to leaf scorch.

'JN31' can also be compared to the co-pending cultivars of *Cercis canadensis* 'JN100', 'JN104', and 'JN106'. 'JN100' differs from 'JN31' in having foliage that emerges bright red and orange that changes to green in color. 'JN104' differs from 'JN31' in having foliage that is dark green in color. 'JN106' differs from 'JN31' in having foliage that emerges burgundy purple that changes to dark green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Website listings include but may not be limited to listings by Garden Debut, Landscapehub, Nursery Guide, Glover Catalog, Site One Landscape Supply, Richardson Roots, Spring Hill Nursery, New Blooms Nursery, Dietrich Gardens, and Weston Nurseries.

BRIEF DESCRIPTION OF THE DRAWINGS

The accompanying color photographs illustrate the overall appearance and distinct characteristics of the new *Cercis*. The photographs were taken of a 4-year-old tree of the new cultivar as grown in a trial garden in Belvidere, Tennessee.

The photograph in FIG. 1 provides a view of the plant habit of 'JN31'.

Figure 1:
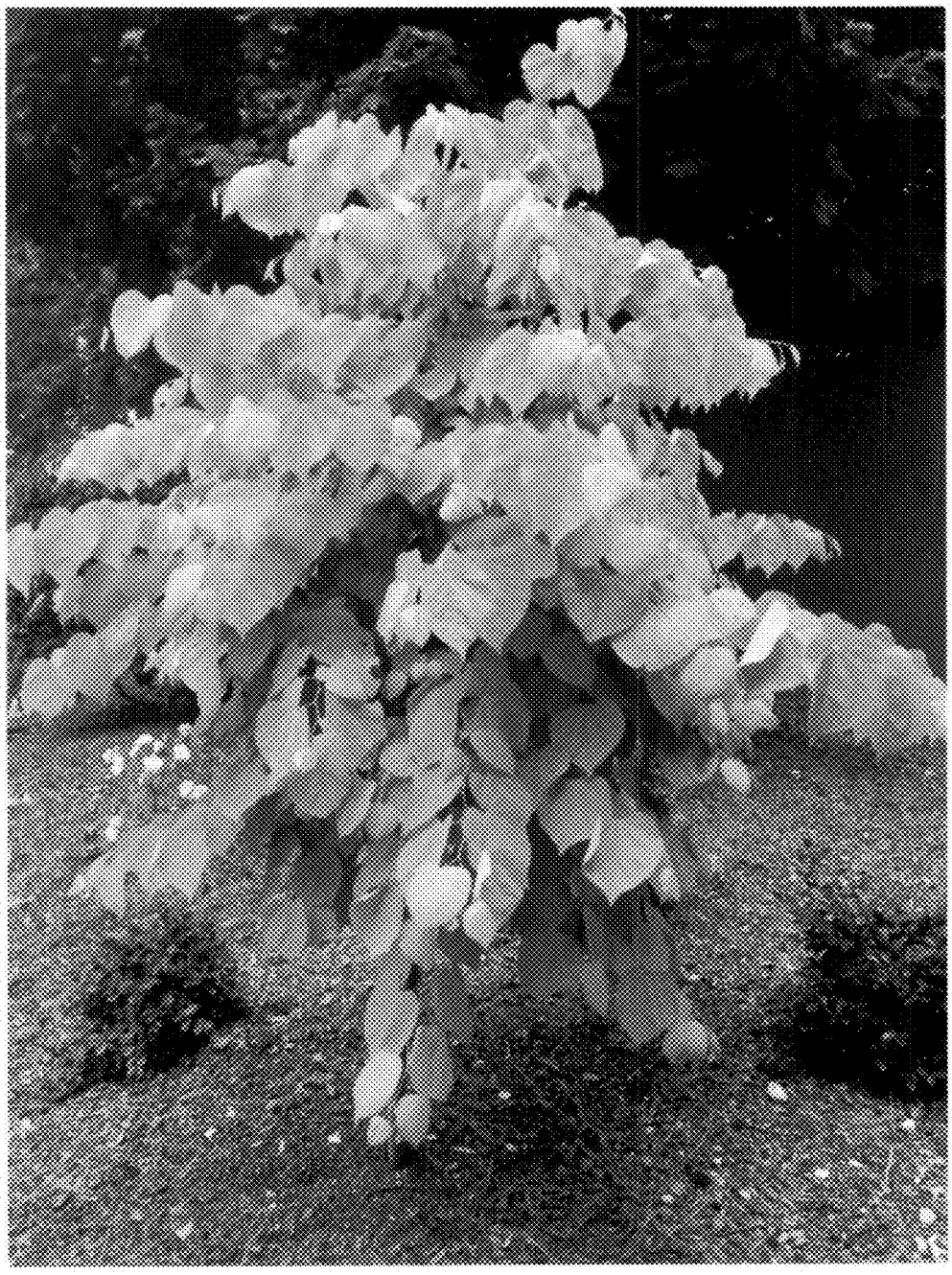
Figure 2:
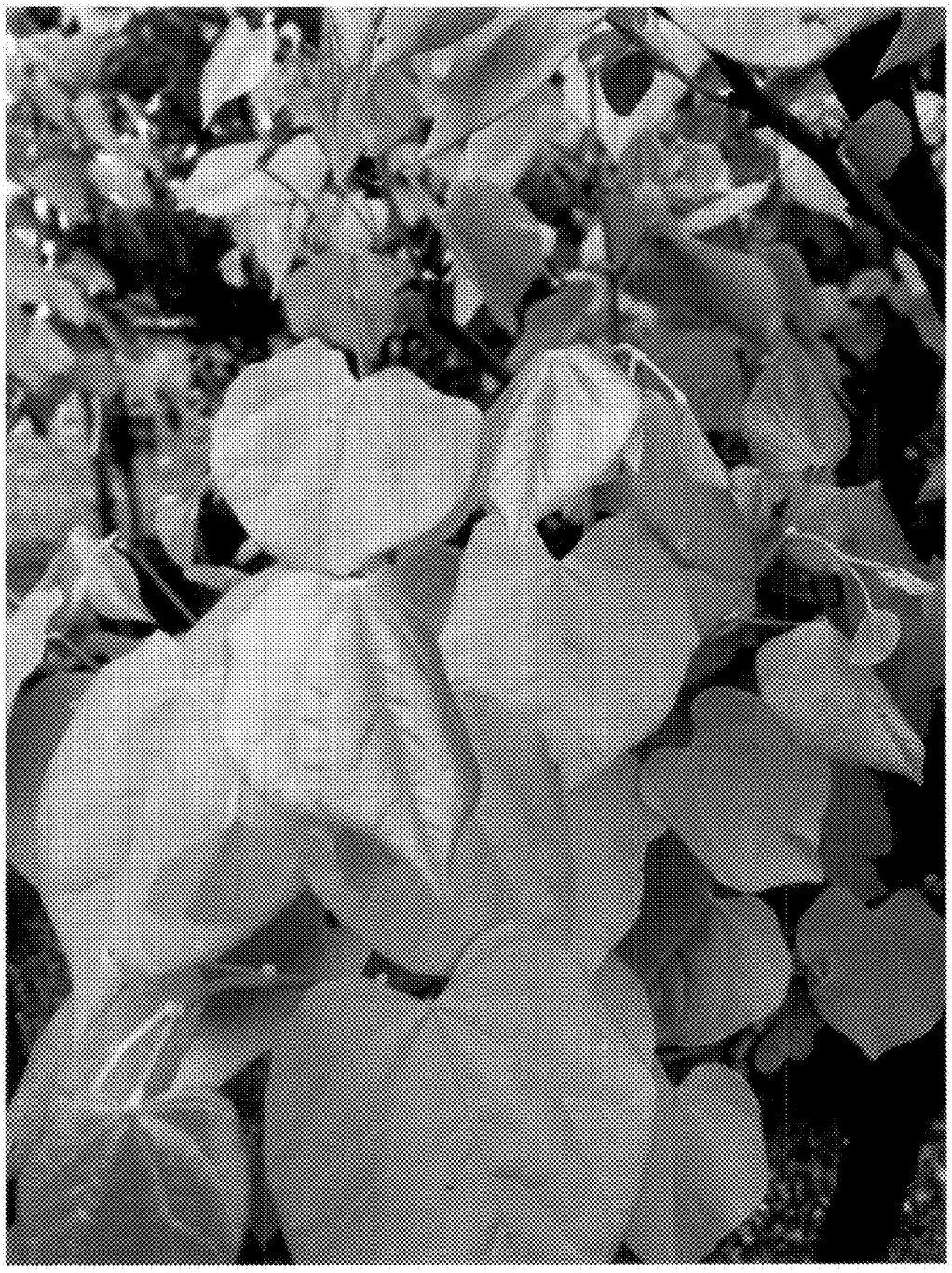

The photograph in FIG. 2 provides a view of the emerging foliage of 'JN31'.

The colors in the photographs are as close as possible with the digital photography techniques available, the color values cited in the detailed botanical description accurately describe the colors of the new *Cercis*.

DETAILED BOTANICAL DESCRIPTION

The following is a detailed description of a 3-year-old plants of the new cultivar as grown in a 5-gallon container in Belvidere, Tennessee. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—3 to 4 weeks in early spring in Belvidere, Tennessee.

*Plant type.*—Deciduous tree.

*Plant habit.*—Upright with strong branches.

*Height and spread.*—Average of 1.2 m in height and 46 cm in width as a 3-year-old tree in a container, as a mature tree reaches between 6 m and 7 m in height and between 4.5 m to 6 m in spread in the landscape.

*Cold hardiness.*—At least to U.S.D.A. Zone 5.

*Diseases and pests.*—No susceptibility or resistance to diseases or pests has been observed.

*Environmental factors.*—Resistant to winter and ice damage and sun scorch when grown in Southern climates.

*Root description.*—Fibrous, 200A in color.

*Propagation.*—Budding.

*Propagation timing.*—Budding in July-August, growth begins in the spring and takes 7 months to become a salable whip.

*Growth rate.*—Moderate.

Branch and trunk description:

*Trunk.*—An average of 2 cm in diameter and 56 cm in length (until lateral branching), surface of bark glabrous, matte, lustrous, relatively smooth, 199A and 199B in color.

*Branch shape.*—Rounded, slightly zig-zag growth habit.

*Branch color.*—New growth, 145A, mature branches; 199A, flushed with 198B.

*Branch size.*—An average of 25 cm in length and 3 cm in width.

*Branch surface.*—Young branches; glabrous, semi-glossy, mature bark; glabrous, matte, lustrous, relatively smooth, lenticels not discernible.

*Internode length.*—An average of 5 cm.

*Branching habit.*—Weeping and zig-zag pattern, 1 main branch, an average of 12 lateral branches per main branch.

Foliage description:

*Leaf shape.*—Orbicular.

*Leaf division.*—Simple.

*Leaf base.*—Cordate.

*Leaf apex.*—Acute to slightly acuminate.

*Leaf fragrance.*—None.

*Leaf venation.*—Palmate, color is not distinguishable from leaf color.

*Leaf margins.*—Entire, slightly undulate.

*Leaf arrangement.*—Alternate.

*Leaf aspect.*—Held reflexed slightly downward from petiole (hanging) to horizontal.

*Leaf attachment.*—Petiolate.

*Leaf number.*—An average of 14 leaves per lateral branch.

*Leaf surface.*—Young; both surfaces very glossy, glabrous, slightly translucent, mature; upper surface is glabrous, velvety, and slightly glossy, lower surface is glabrous and matte.

*Leaf size.*—An average of 7.5 cm in length and 9 cm in width. Leaf color.—Emerging; 150C, flushed with 177B and 181A, young; both surfaces N144A, mature; upper surface 144A to 144B, slightly tinged N144A, lower surface a blend of 145A and 144C, fall color; a color between 162A and 20A on both surfaces.

*Petiole.*—An average of 2 cm in length and 1.5 mm in width, glabrous and glossy surface, flexible and moderately strong, 145A, flushed with 182B.

Inflorescence description:

*Inflorescence type.*—Cauliflorous clusters of papilionaceous (pea-like) flowers.

*Inflorescence size.*—Up to 4 cm in width and 3.5 cm in depth.

*Lastingness of inflorescence.*—2 to 3 weeks.

*Flower size*.—An average of 1.2 cm in length and width.

*Flower fragrance*.—Faint.

*Flower number*.—An average of 8 flowers per cluster.

*Bracts*.—Average of 7, surrounding base of inflorescence, whorled, imbricate, ovate in shape, acute apex, an average of 0.75 mm in length and width, color; 200A, glabrous and matte surfaces.

*Peduncles*.—An average of 1.8 cm in length and 0.5 mm in diameter, color; 187C, slightly glossy surface, moderately strong, held straight from base to slightly curved, held at all directions from branch node in a whorled arrangement.

*Pedicels*.—None, peduncles attached in cluster at branch.

*Flower buds*.—Slightly curved, beak-shaped, 8 mm in length, 3 mm in width, glabrous and matte surfaces, color; 77B.

*Flower type*.—Papilionaceous.

*Calyx*.—Campanulate in shape, 4 mm in length, 3.5 mm in diameter.

*Sepals*.—5, 95% of base fused, 3 mm in length, free part of sepal 1 mm in length and width, bluntly acute apex, entire margins, both surfaces are glabrous and matte, both surfaces 187A in color.

*Corolla features*.—Papilionaceous, bilateral with two upper petals around the stamens and pistil, a center petal, and two lower petals under the center petal, upper petals; elliptic and cup shaped, margins slightly undulate, average of 9 mm in length, 6 mm in width, both surfaces glabrous, slightly glossy, color when opening and fully open; N78A, N78C, base 84D, fading to 91A, center petal; 2 mm in length, 3 mm in width, both surfaces glabrous, slightly glossy, broad in shape and curled downward, rounded apex, cuneate base, entire margins, slightly undulate, color when opening and fully open; N78A, N78C, base 84D, fading to 91A, lower petals; elliptical to in shape, curled downward, margins moderately undulate, average of 8.5 mm in length, 3 mm in width, both surfaces glabrous, slightly glossy and slightly transparent at the base, color when opening and fully open; N78A, N78C, base 84D, fading to 91A.

Reproductive organs:

*Gynoecium*.—Pistil; 1, stigma; very small, round, 0.3 mm in diameter, 19C in color, slightly transparent, style; an average of 8 mm in length, 1 mm in width, 61A in color, ovary; round, in bottom of calyx, N92A in color.

*Androecium*.—Stamens; 10, anthers; oval shaped, an average of 0.8 mm in diameter, 200A in color, filament; an average of 5 mm in length and 0.8 mm in width, color; N80B, glossy and transparent surface, pollen is abundant in quantity, 19C in color.

*Seed and fruit*.—None observed to date.

It is claimed:

1. A new and distinct cultivar of *Cercis canadensis* tree named 'JN31' as herein illustrated and described.

* * * * *